United States Patent
Güngör Reis et al.

(10) Patent No.: US 10,617,136 B2
(45) Date of Patent: Apr. 14, 2020

(54) CALCIUM OXIDE COMPOUND WITH HIGH PURITY

(71) Applicant: ARKIM KIMYEVI MADDELER SANAYI VE TICARET ANONIM SIRKETI, Istanbul (TR)

(72) Inventors: Elif Güngör Reis, Istanbul (TR); Muzaffer Yaşar, Istanbul (TR); Leyla Türker Şener, Istanbul (TR)

(73) Assignee: ARKIM KIMYEVI MADDELER SANAYI VE TICARET ANONIM SIRKETI, Istanbul (TR)

( * ) Notice: Subject to any disclaimer, the term of this patent is extended or adjusted under 35 U.S.C. 154(b) by 290 days.

(21) Appl. No.: 15/520,068

(22) PCT Filed: Dec. 15, 2015

(86) PCT No.: PCT/TR2015/000360
§ 371 (c)(1),
(2) Date: Apr. 18, 2017

(87) PCT Pub. No.: WO2016/108778
PCT Pub. Date: Jul. 7, 2016

(65) Prior Publication Data
US 2017/0325486 A1    Nov. 16, 2017

(30) Foreign Application Priority Data
Dec. 29, 2014 (TR) .............. a 2014 016045

(51) Int. Cl.
| | | |
|---|---|---|
| *C01F 11/06* | (2006.01) |
| *A23L 3/358* | (2006.01) |
| *A23L 33/16* | (2016.01) |
| *A23B 9/30* | (2006.01) |
| *A01N 59/06* | (2006.01) |
| *A61K 33/08* | (2006.01) |
| *A23L 7/157* | (2016.01) |

(52) U.S. Cl.
CPC .............. *A23L 3/358* (2013.01); *A01N 59/06* (2013.01); *A23B 9/30* (2013.01); *A23L 7/157* (2016.08); *A23L 33/16* (2016.08); *A61K 33/08* (2013.01); *C01F 11/06* (2013.01); *C01P 2006/80* (2013.01); *Y02A 50/473* (2018.01)

(58) Field of Classification Search
CPC ....................................................... C01F 11/06
See application file for complete search history.

(56) References Cited

FOREIGN PATENT DOCUMENTS

| | | |
|---|---|---|
| JP | 2003026525 A | 1/2003 |
| WO | WO2004105912 A2 | 12/2004 |
| WO | WO2007033684 A1 | 3/2007 |
| WO | WO2012054409 A1 | 4/2012 |

*Primary Examiner* — Stuart L Hendrickson
(74) *Attorney, Agent, or Firm* — Bayramoglu Law Offices LLC

(57) ABSTRACT

This invention is about calcium oxide. The invention relates more particularly to obtaining the calcium oxide with high purity and on the implementation.

4 Claims, 11 Drawing Sheets

CALCIUM OXIDE COMPOUND WITH HIGH PURITY

CROSS REFERENCE TO RELATED APPLICATIONS

This application is the national phase of International Application No. PCT/TR2015/000360, filed on Dec. 15, 2015, which is based upon and claims priority to Turkish Patent Application No. 2014/16045, filed on Dec. 29, 2014, the entire contents of which are incorporated herein by reference.

THE TECHNICAL FIELD OF THE INVENTION

This invention is about calcium oxide. The invention relates more particularly to obtaining the calcium oxide with high purity and on the implementation.

BACKGROUND

Calcium oxide (CaO) or hydrated lime is a kind of chemical compound having a wide field of use. It is a white, caustic and alkaline solid. In industry, it is obtained with removing carbon dioxide by melting the limestone at high temperatures. It is oxidized when reacted with water and thus calcium hydroxide is formed. It is a compound having ionic bond.

Calcium oxide is widely used in industry, e.g., binders in construction mortars and plasters, purifying in iron and steel industry, pH modifier for rehabilitation of acidic soils, intermediate product or final product component in preparation of various chemical materials, additive in road surface construction and in many other areas.

Metal oxides are especially known with their antibacterial properties. These properties point out to new usage areas of metal oxides. It seems possible in these areas may be related to medical applications such as food.

The food that offered to the consumer at present contain lots of chemicals except the main components. These chemical substances are classified as carbohydrates, lipids, proteins, vitamins and minerals. Food security can be defined as adequate for balanced nutrition, sustainable, economically accessible and healthy food supply to people. Increasing food production, preventing the loss of produced food, storage while maintaining the quality of the food and extension of shelf life are gaining importance for ensuring food security. In this case, production and consumption relations of foods make a technological necessity the using of additives. Nevertheless, recent researches show that additives can create risks for consumers. Using of these substances was restricted as a result of many research.

Food additives can be synthetic or natural origin. In particular, doubts about harmful effects of synthetic food additives to human health is extremely strong. Especially, the preservative used to prolong the shelf life of any food is considered to pose a risk to human health. However, it is clear that the need for food with a long shelf life when considering the present level of population growth and food supply. Most commonly used additives in prolonging the shelf life of food are sodium benzoate, potassium sorbate and sodium metabisulphite. But, it carries all doubts on the reliability of these products for human health. Therefore, it is of vital importance using additive for food which was known as obtained from natural sources and not harmful to human body. In addition, purity levels of natural origin substances of this type is very important. Briefly, requirements of food industry toward additives which have high purity and also known as reliable in terms of health is too much. In food codex, E-529 known as calcium oxide (CaO) is used as acidity regulator and anti-caking. There is also no known side effects. However, purity of the calcium oxide for food applications is not at the desired level, and the existing ones enforce the usage limits in terms of economical.

In addition, the high confidence interval of calcium oxide may lead to new approaches to disease treatment area. But, there is no adequate research and application in medical practice.

Owing to these disadvantages, it is clear that there is need for new approaches for in technical fields related to calcium oxide, reliability, ease of access, food and medical applications and innovation is required.

SUMMARY OF THE INVENTION

The present invention eliminates all the problems mentioned above and bringing additional advantages to the relevant technical field which relates to high purity new calcium oxide compound, process for preparing this compound and applications of it in food and health area.

The main object of the invention is particularly obtaining of calcium oxide compound with high purity.

Another object of the invention is the development of a method for obtaining high purity calcium oxide compound.

Another object of the invention may be used of calcium oxide compound in high purity as preservatives in foods.

Another object of the invention may be used as therapeutic of calcium oxide compound in high purity.

To achieve all the objectives mentioned above and can be seen from the following detailed description, a new calcium oxide compound was obtained.

A novelty that mentioned in a preferred application of the invention, the amount of the minerals which is forming impurities for stated compound must be as follows:

Sulfur≤1 ppm,
Nickel≤1 ppm,
Arsenic≤1 ppm,
Antimony≤1 ppm,
Lead≤1 ppm,
Mercury≤1 ppm,
Silicon≤1 ppm.

In another preferred application of the invention, mentioned calcium oxide compound is 99%.

Another preferred application of the invention relates to calcium oxide production method and including the following steps:

I. Washing and drying of the natural calcium oxide source,
II. Vibratory ball mill grinding of natural calcium oxide source,
III. Calcination of natural calcium oxide source in the rotary kiln using platinum as a catalyst and nitrogen as a forming inert atmosphere at 700-1200° C. for 1-3 hours.

Another preferred application of the invention relates to calcium oxide production method and including the following steps:

IV. Washing and drying of the natural calcium oxide source,
V. Vibratory ball mill grinding of natural calcium oxide source,
VI. Calcination of natural calcium oxide source in the rotary kiln using platinum as a catalyst and nitrogen as a forming inert atmosphere at 1000-1400° C. for 1.5-2.5 hours.

Another preferred application of the invention relates to calcium oxide production method and including the following steps:

VII. Washing and drying of the natural calcium oxide source,
VIII. Vibratory ball mill grinding of natural calcium oxide source,
IX. Calcination of natural calcium oxide source in the rotary kiln using platinum as a catalyst and nitrogen as a forming inert atmosphere at 1150-1250° C. for 1 hour 45 minutes-2 hours 15 minutes.

Another preferred application of the invention relates to calcium oxide production method and including the following steps:

X. Washing and drying of the natural calcium oxide source,
XI. Vibratory ball mill grinding of natural calcium oxide source,
XII. Calcination of natural calcium oxide source in the rotary kiln using platinum as a catalyst and nitrogen as a forming inert atmosphere at 1200° C. for 2 hours.

Another preferred application of the invention relates to calcium oxide production method and this compound is obtained by calcination of natural calcium oxide source at 1200° C. for 2 hours.

Another preferred application of the invention, calcium oxide used as preservatives in foods.

Another preferred application of the invention, solution of calcium oxide compound of by weight 0.1%-10% is used as preservative in foods.

Another preferred application of the invention, solution of calcium oxide compound of by weight preferably 0.1%-2% is used as preservative in foods.

Another preferred application of the invention, solution of calcium oxide compound of by weight more preferably 0.4% is used as preservative in foods.

Another preferred application of the invention, the food which of the mentioned compound is used as preservative is selected from one of the solid or liquid form foods containing meat, milk, flour, nuts, vegetables and fruits.

Another preferred application of the invention relates to calcium oxide, in mammals, especially in humans is for preventing or treating cancer.

Another preferred application of the invention is using of mentioned compound as an antibacterial for *Staphylococcus aureus, Enterobacter aerogenes, Enterococcus Klebsiella pneumonia* and *Escherichia coli* in foods.

Another preferred application of the invention relates to calcium oxide, in mammals, especially in humans is for preventing or treating breast cancer.

DETAILED DESCRIPTION OF THE INVENTION

Materials and Methods

Figure 1:
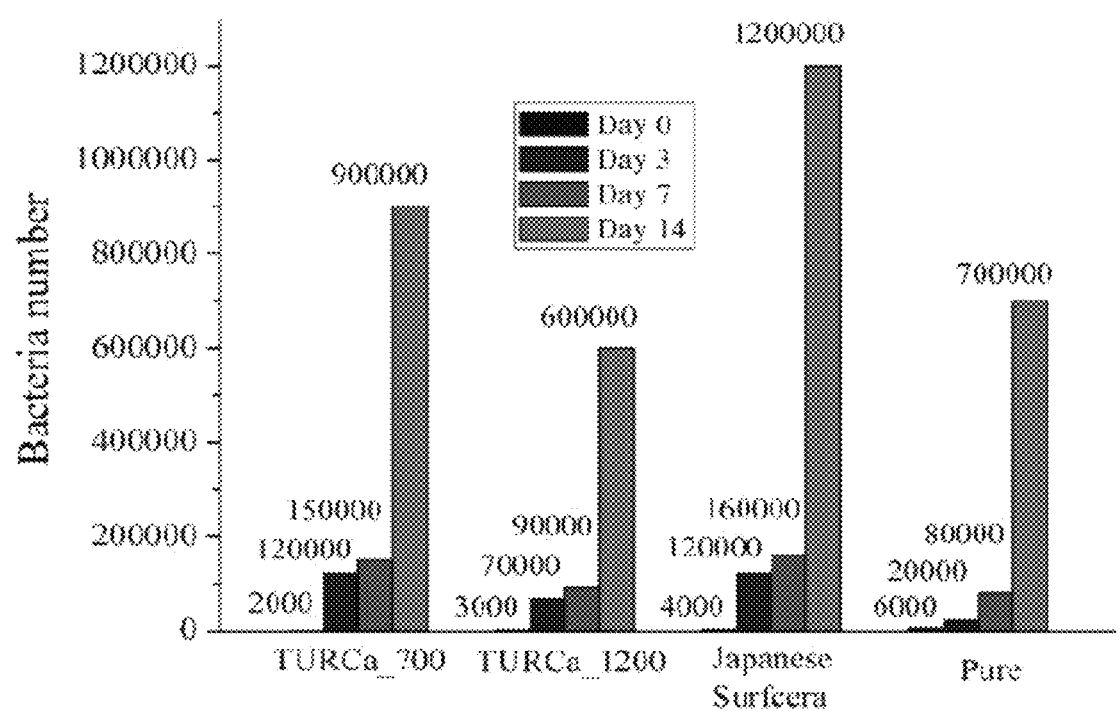
FIG. 1 is a graph which shows the antibacterial activity in the cheese samples containing calcium oxides mentioned in the invention, surfcera and the cheese sample without additives.

In the mentioned invention, egg shell is thoroughly washed several times and dried in an oven at 200° C. to remove moisture. Then, the shell is ground in a vibratory ball mill with a suitable vibration rate. Antibacterial agent is obtained with calcination of egg shell. Calcination of egg shell is carried out in the rotary kiln at 500-1400° C., preferably 700-1200° C., for 1-3 hours, preferably 2 hours, using platinum as a catalyst and nitrogen as a forming inert atmosphere. By this process, organic parts of the shell are removed and a white calcined substance is come out. Nitrogen provide an inert medium. The mentioned product was prepared at two different temperatures including 700° C. and 1200° C. named as Sample 1 and Sample 2, respectively. Moreover, the effectiveness of the samples are compared with the Japan based product named commercially as Surfcera. The elemental composition of Sample 2 is determined with the Wavelength Dispersive X-ray Fluorescence Spectrometry (XDXRF). The composition analysis table of Sample 2 is as follows:

| Element | Amount (ppm) |
| --- | --- |
| Calcium | <700 000 |
| Sulfur | <25 |
| Phosphorus | <1500 |
| Nickel | <1 |
| Arsenic | <1 |
| Antimony | <1 |
| Lead | <1 |
| Mercury | <1 |
| Strontium | <40 |
| Selenium | <1 |
| Silver | <10 |

-continued

| Element | Amount (ppm) |
| --- | --- |
| Sodium | <100 |
| Aluminum | <5 |
| Magnesium | <4000 |
| Tin | <20 |
| Potassium | <150 |
| Manganese | <1 |
| Barium | <5 |
| Silicon | <1 |
| Cadmium | <1 |
| Chromium | <1 |
| Vanadium | <1 |
| Cobalt | <1 |
| Copper | <10 |
| Zinc | <1 |
| Iron | <10 |

Sample 1 is the calcium oxide obtained from calcination of egg shell at 700° C. for 2 hours.

Sample 2 is the calcium oxide obtained from calcination of egg shell at 700° C. 2 hours.

Natural calcium oxide source contains especial egg shell, oyster shell and mussel shell.

In order to critical important minerals within the mentioned calcium oxide, the following values are given as the maximum amount of impurities.

Sulfur≤1 ppm,
Nickel≤1 ppm,
Arsenic≤1 ppm,
Antimony≤1 ppm,
Lead≤1 ppm,
Mercury≤1 ppm,
Silicon≤1 ppm.

Examining of Antibacterial Activity

It is examined the antibacterial effect of mentioned calcium oxide in various foods. Solution of mentioned product may be prepared by using one of water, aqueous ethanol, glucose, glycerin, isopropyl alcohol, polyethylene glycol or mixtures thereof. Also, it can be prepared using other non-deleterious solvents for human health. The solution may be prepared in by weight 0.01% to 10% and used. The preferred amount of solution is 0.1%-2%. Mentioned product can be used in products such as meat, milk, flour, vegetables and fruits, nuts and is also used in cosmetic products and drugs as antimicrobial and antifungal. Furthermore, using of the product is also valid for crude, intermediate and final form of these products. When the spray solution of mentioned product is applied to the surface of fruits and vegetables, it prevents harmful agents to human health and also provides long-term protection of their freshness.

During the implementation phase, solutions by weight 0.1% to 4% of Sample 1 and Sample 2 were prepared. Also, it can be used as dispersed in practice. Mentioned calcium oxide applied on bread, pasta, water, feta cheese, cheddar cheese, cottage cheese, olive, tomato, cucumber, egg, meat, chicken, salami, mayonnaise, butter, cabbage, potato, mandarin, chips and effect was demonstrated. Although Sample 2 contains 99% calcium oxide, also it has a variety of minerals. pH of saturated solution of Sample 2 is 12-13.

Dairy Products

Equal amounts of cheese, feta cheese, mayonnaise, cottage cheese and butter is kept in 0.4% of aqueous solution of Sample 1, Sample 2 and Japanese Surfcera at 21° C. for 0, 3, 7, 14 days and then, bacterial counts were made. Studied bacteria are *Escherichia coli, Staphylococcus aureus* ve *enterococcus*. Bacteria amounts were observed in all examples day by day. In the presence of Sample 1 and Sample 2, 900 000 and 600 000 bacteria are observed at the end of 14 days, respectively. When used Japanese Surfcera, 1 200 000 bacteria were found. On the other hand, 700 000 bacteria were determined in the sample without any additives which placed in pure water. As a result, Sample 2 (calcium oxide produced at 1200° C.) exhibited higher antibacterial activity than other sample. Antibacterial activity on cheese is shown in FIG. 1.

Figure 2:
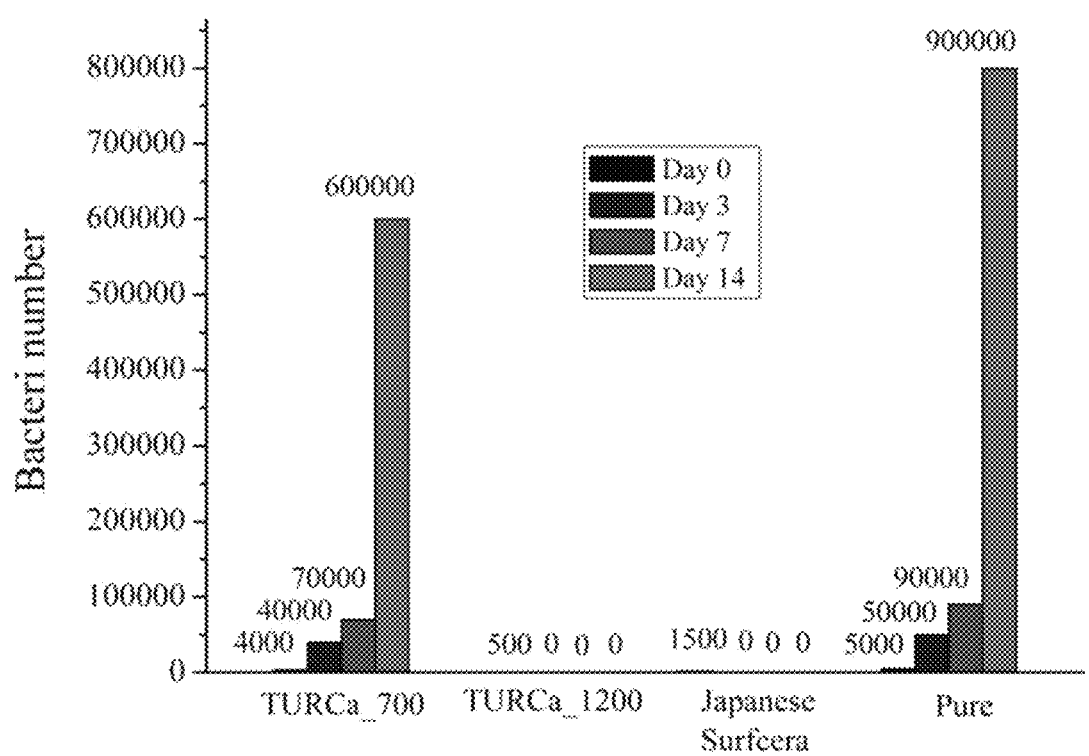
FIG. 2 is a graph which shows the antibacterial activity in the feta cheese samples containing calcium oxides mentioned in the invention, surfcera and the feta cheese sample without additives.

FIG. 2 shows the antibacterial activity on feta cheese. In the presence of Sample 2, there have been no bacterial growth at the end of 14 days. When used Japanese Surfcera, bacteria occurs only the first day and then all bacteria are destroyed. Moreover, Sample 1 and pure sample are used, the number of bacteria increased day by day. At the end of 14 days, 600 000 and 900 000 bacteria were seen with Sample 1 and pure sample, respectively.

Furthermore, same tests were carried out using cottage cheese, mayonnaise and butter. According to results of these three milk products, in the presence of Sample 1, Sample 2 and Japanese Surfcera, there have been no bacterial growth at the end of 14 days. Besides, in the pure sample of mayonnaise, cottage cheese and butter, 900 000, 1 200 000 and 1200 bacteria were detected, respectively. It is seen that bacterial growth began in the seventh day for mayonnaise, in the first day for cottage cheese and in the fourteenth day for butter.

Bakery Products

Equal amounts of boiled pasta, bran bread and pie is kept in 0.4% of aqueous solution of Sample 1, Sample 2 and Japanese Surfcera at 21° C. for 0, 3, 7, 14 days and then, bacterial counts were made. *Staphylococcus aureus* ve *enterococcus* were observed in all examples.

Figure 3:
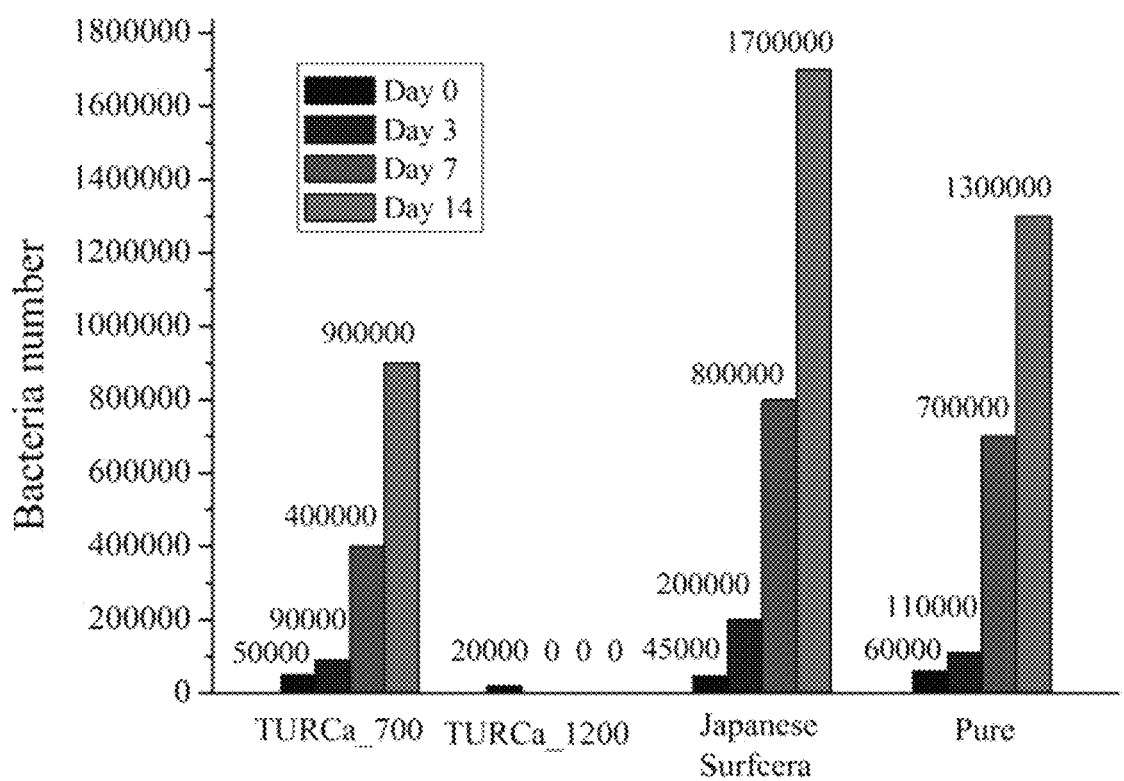
FIG. 3 is a graph which shows the antibacterial activity in the boiled pasta samples containing calcium oxides mentioned in the invention, surfcera and the boiled pasta sample without additives.

Antibacterial test results of boiled pasta is shown in FIG. 3. When used Sample 2, bacteria occurs only the first day and then all bacteria are destroyed. In the presence of Sample 1, Japanese Surfcera and pure sample, 900 000, 1 700 000 and 1 300 000 bacteria are observed at the end of 14 days, respectively. Apparently, Sample 2 exhibited the best antibacterial activity with boiled pasta.

Figure 4:
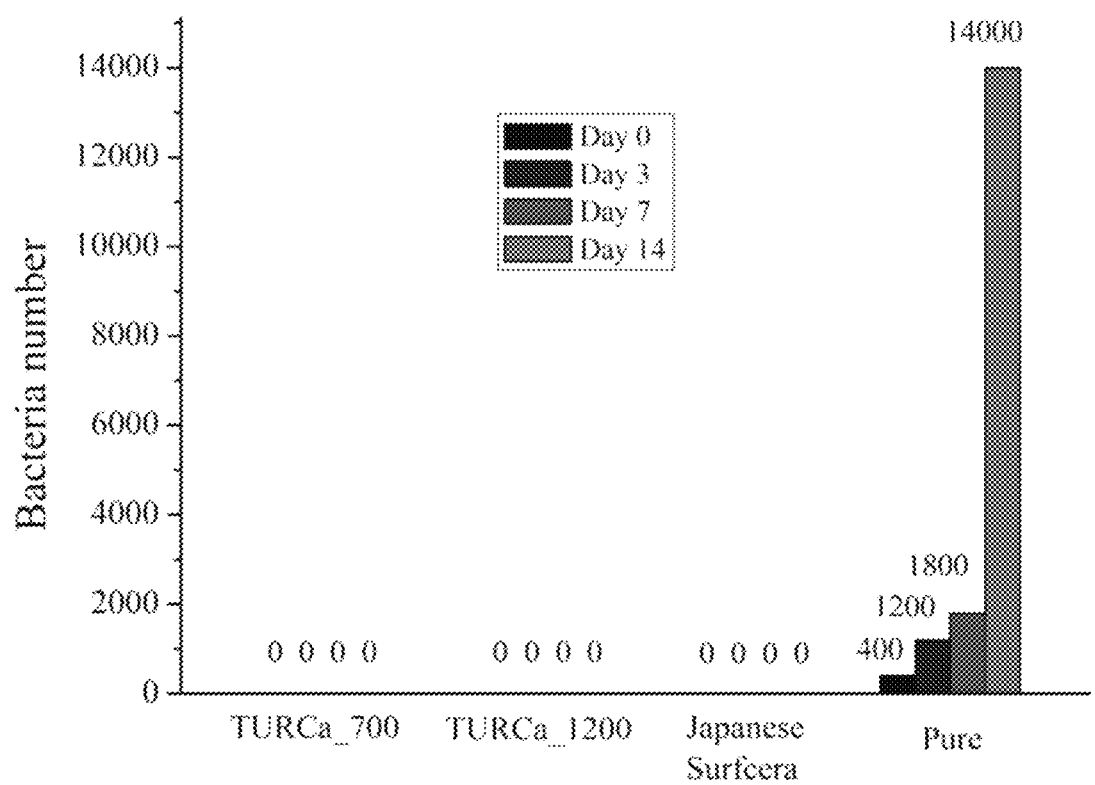
FIG. 4 is a graph which shows the antibacterial activity in the bran bread samples containing calcium oxides mentioned in the invention, surfcera and the bran bread sample without additives.

The samples was also tested with bran bread at same conditions. As seen in FIG. 4, in the presence of Sample 1, Sample 2 and Japanese Surfcera, bacterial growth was not observed for 14 days. Besides, in the pure sample of bran bread 14 000 bacteria were detected at the end of 14 days.

Antibacterial tests were performed with pie. Bacterial growth was only appeared in pure sample and 160 000 bacteria was detected at the end of 14 days.

As comparison, Sample 2 and pure sample were used to carry out the microbiological tests on bran brad at 37° C. for 7 days. The results have shown that there have been no bacterial growth with Sample 2. On the other hand, when used pure sample, 1 200 000 bacteria were occurred at the end of 7 days.

Meat Products

Equal amounts of meat, fish and salami is kept in 0.4% of aqueous solution of Sample 1, Sample 2 and Japanese Surfcera at 21° C. for 0, 3, 7, 14 days and then, bacterial counts were made. *Staphylococcus aureus* and *Enterobacter aerogenes* were observed in fish and salmon. Also, *Escherichia coli* and *Enterococcus* were occurred in meat.

Figure 5:
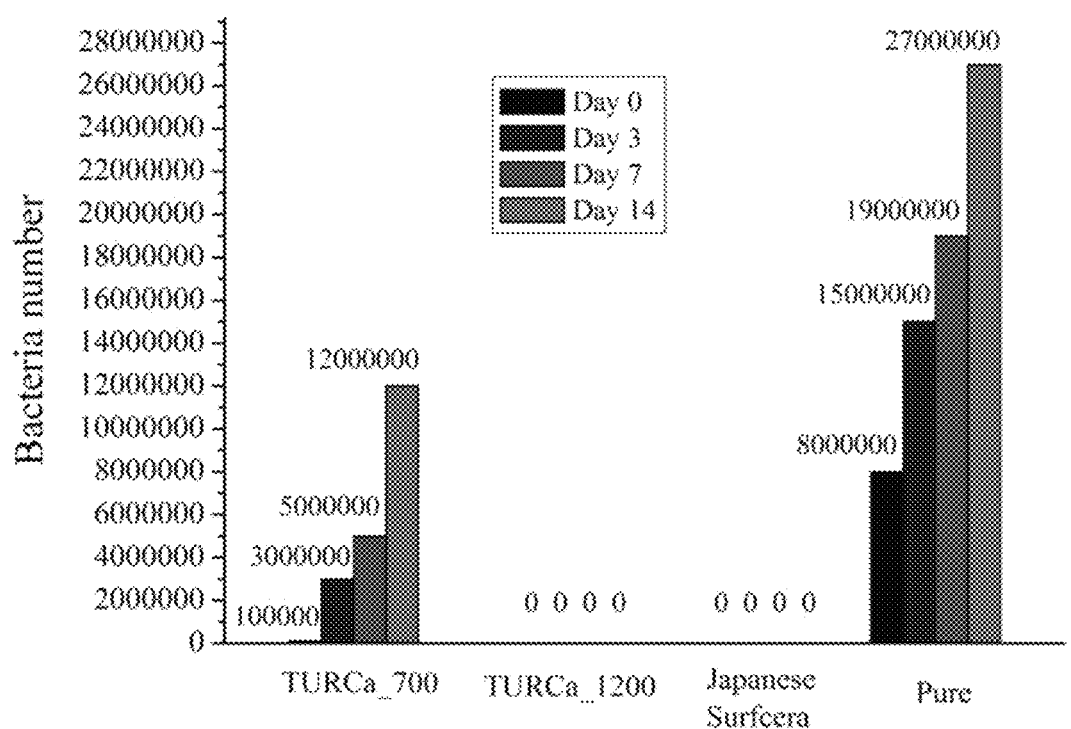
FIG. 5 is a graph which shows the antibacterial activity in the meat samples containing calcium oxides mentioned in the invention, surfcera and the meat sample without additives.

Antibacterial test results of meat is shown in FIG. 5. In the presence of Sample 2 and Japanese Surfcera, bacterial growth was not observed for 14 days. Besides, when used pure sample and Sample 1, 27 000 000 and 12 000 000 bacteria were occurred at the end of 14 days, respectively.

Antibacterial tests were also performed with fish and salami under same conditions. There is no any bacterial growth with Sample 1, Sample 2 and Japanese Surfcera.

Bacterial growth was only appeared in pure samples and 30 000 000 and 28 000 000 bacteria was detected for fish and salmon, respectively.

Figure 6:
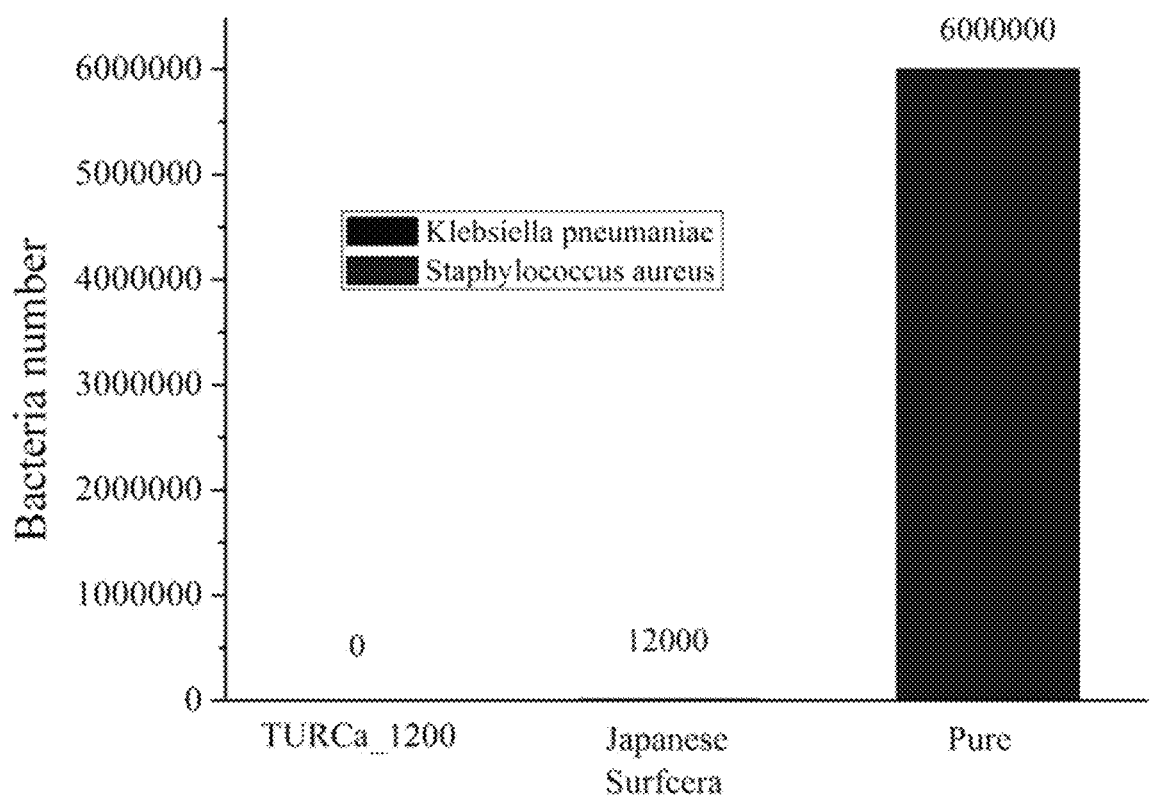
FIG. 6 is a graph which shows the antibacterial activity in the salami samples containing calcium oxides mentioned in the invention, surfcera and the salami sample without additives.

For comparison purposes, Sample 2, Japanese surfcera and pure sample were used to carry out the microbiological tests on salami at 37° C. for 7 days. As seen in FIG. 6, there have been no bacterial growth when used Sample 2. On the other hand, 12 000 *Klebsiella pneumonia* and 6 000 000 *Staphylococcus aureus* were consisted in the presence of Japanese surfcera and pure samples, respectively. Apparently, Sample 2 is more effective than others.

Fruits and Vegetables

Equal amounts of mandarin, zucchini, potato, tomato, tomato paste, cucumber, olive and white cabbage is kept in 0.4% of aqueous solution of Sample 1, Sample 2 and Japanese Surfcera at 21° C. for 0, 3, 7, 14 days and then, bacterial counts were made. *Staphylococcus aureus, Enterobacter aerogenes, Enterococcus* and *Klebsiella pneumonia* were observed in fruits and vegetables.

Figure 7:
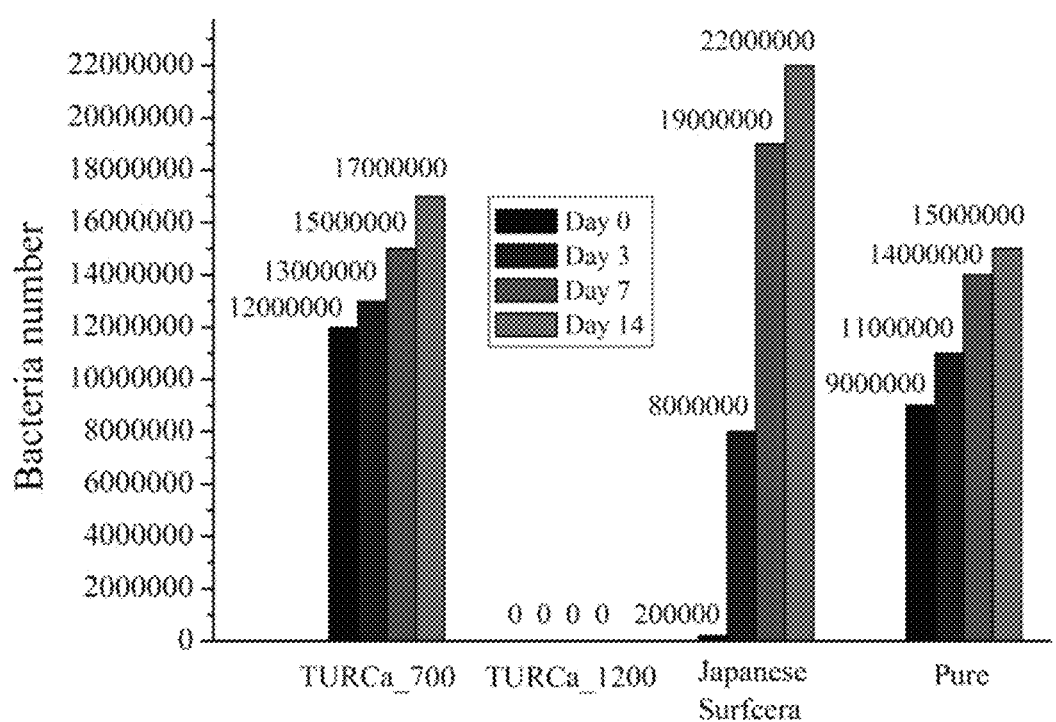
FIG. 7 is a graph which shows the antibacterial activity in the mandarin samples containing calcium oxides mentioned in the invention, surfcera and the mandarin sample without additives.

Antibacterial test results of mandarin is shown in FIG. 7. *Staphylococcus aureus, Enterobacter aerogenes* and *Enterococcus* were consisted over mandarin. In the presence of Sample 1, Japanese Surfcera and pure sample, 17 000 000, 22 000 000 and 15 000 000 bacteria are observed at the end of 14 days, respectively. When used Sample 2, there have been no bacterial growth. Apparently, Sample 2 exhibited the best antibacterial activity with mandarin.

Figure 8:
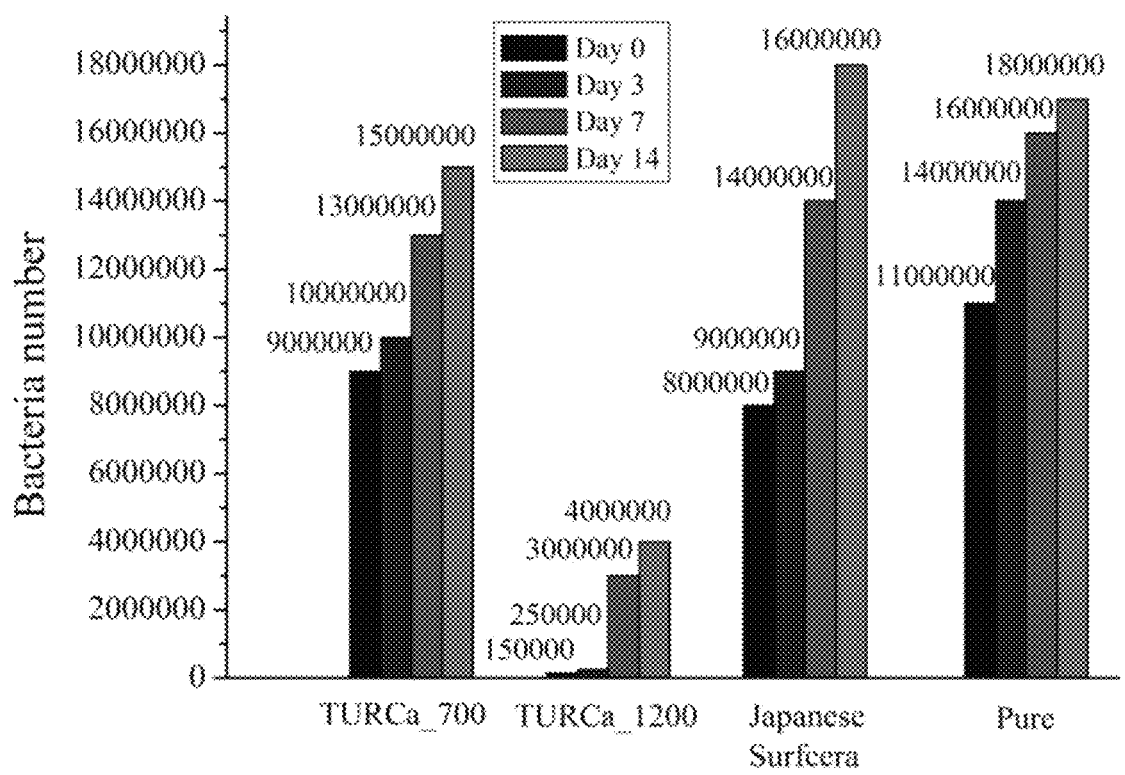
FIG. 8 is a graph which shows the antibacterial activity in the zucchini samples containing calcium oxides mentioned in the invention, surfcera and the zucchini sample without additives.

According to test results made with zucchini, bacterial growth increases day by day in all samples, as shown in FIG. 8. *Klebsiella pneumonia* and *Staphylococcus aureus* occurred over zucchini. When used Sample 1, Sample 2, Japanese Surfcera and pure sample, 15 000 000, 4 000 000, 18 000 000 and 17 000 000 bacterial growth realized at the end of 14 days, respectively. Obviously, Sample 2 is more effective than others as an antibacterial and the worst is Japanese Surfcera.

Figure 9:
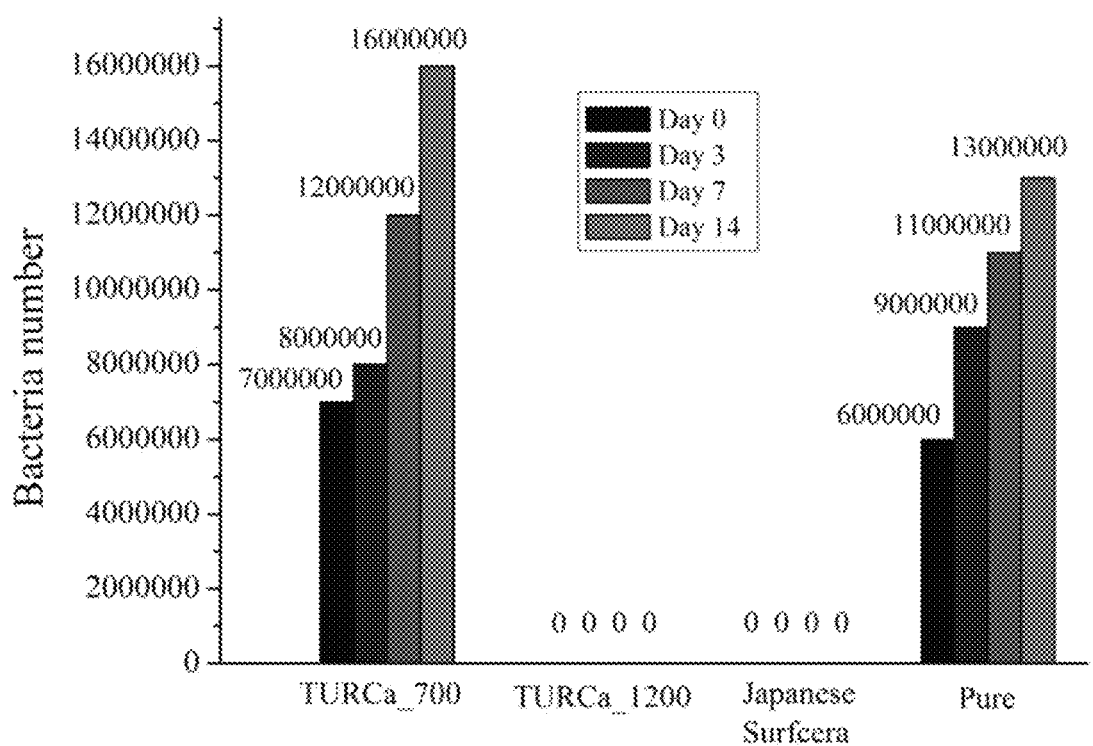
FIG. 9 is a graph which shows the antibacterial activity in the potato samples containing calcium oxides mentioned in the invention, surfcera and the potato sample without additives.

FIG. 9 shows the antibacterial test results made with potato. *Staphylococcus aureus* and *Enterococcus* occurred over potato. In the presence of Sample 1 and pure sample, 16 000 000 and 13 000 000 bacteria was observed at the end of 14 days, respectively. When used Sample 2 and Japanese Surfcera, there have been no bacterial growth over potato.

Antibacterial tests were also performed with tomato, tomato paste, cucumber, olive and white cabbage under same conditions. There is no any bacterial growth with Sample 1, Sample 2 and Japanese Surfcera. Bacterial growth was only appeared in pure samples and a significant amount of bacteria was determined.

Cancer Cells

Cell Culture:

MDA-MB-231 breast cancer cells were cultured in DMEM/F12 medium containing 2 mM L-glutamine, 10% FBS, 1% (v/v) antibiotics.

Figure 10:
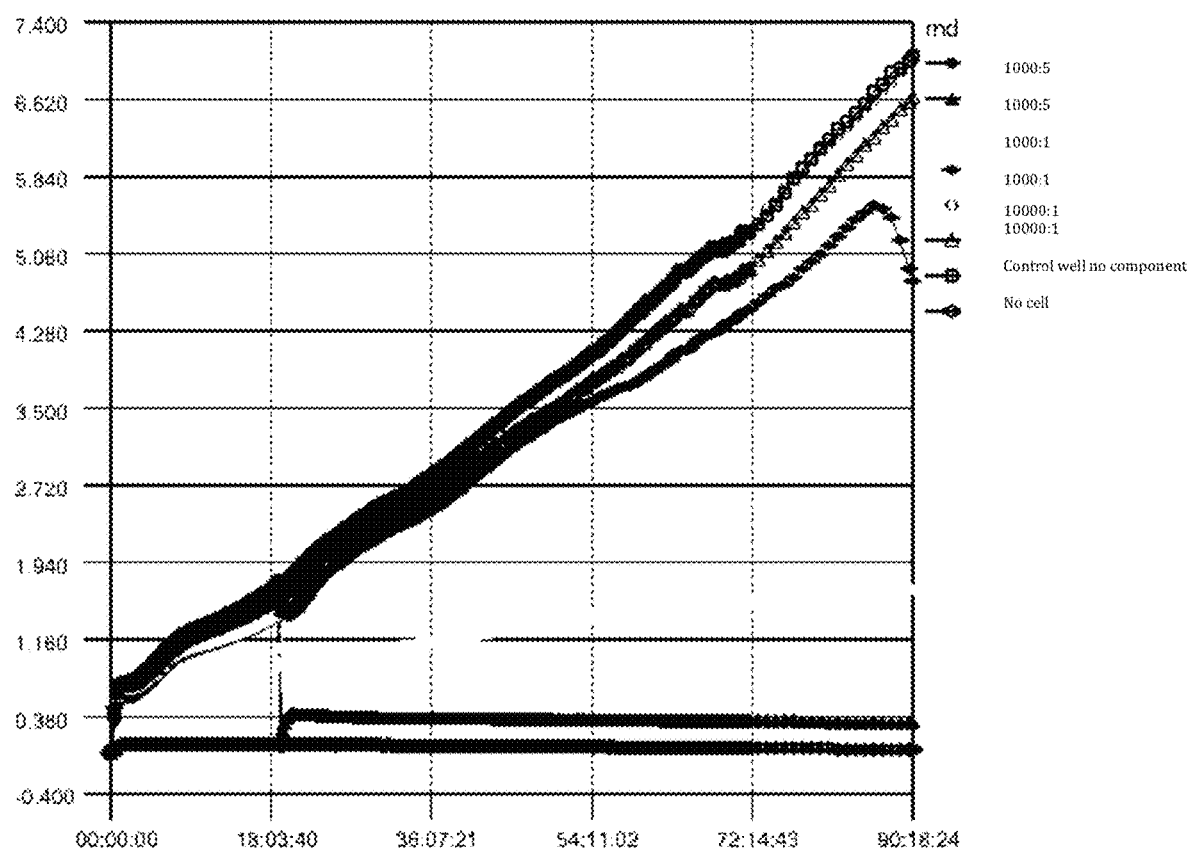
FIG. 10 is a graph which shows the activity of calcium oxide mentioned in the invention on cancer cells.
Figure 11:
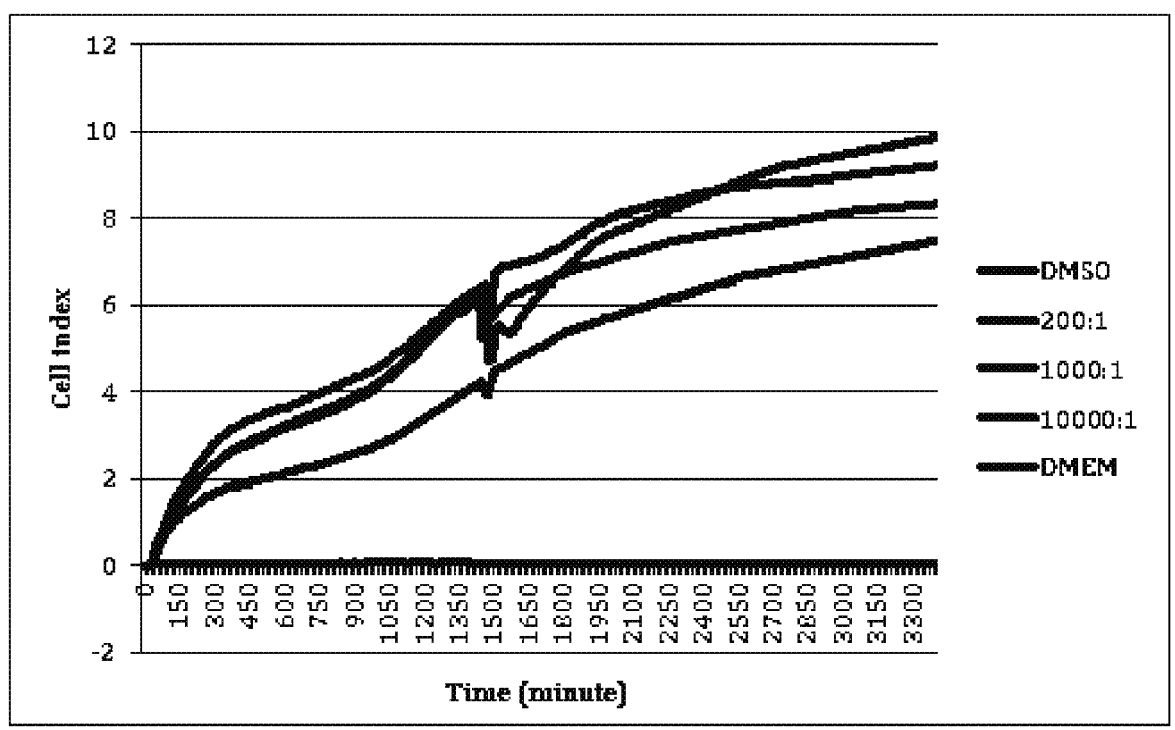
FIG. 11 is a graph which shows the calcium oxide mentioned in the invention does not contain toxic effect on healthy cells.

Measurement of Cytotoxic Activity with Icelligence System:

MDA-MB-231 breast cancer cell line (10000 cell/well) seeded onto 8-well special plate belonging to the icelligence system. Different doses of the sample (1000:5, 1000:1, 10 000:1) were prepared stopping device at twentieth hour as indicated in FIG. 10 and applied to the cells. After application, the two repeated measurements have been made with 15-minute intervals for 72 hours. The same results were obtained at all repeats and controls.

Accordingly, in the tests carried out in different concentrations, when the application held at 0.05% dose (1000:5), vital activity of existing cancer cells has ended at that moment applied. In the more dilute doses, it did not show any toxic effects on breast cancer cells.

As an astonishing result, antibacterial agent was obtained from the egg shell by calcination reaction. The temperature of the calcination process is significant for the activity of mentioned calcium oxide. Especially, calcium oxide obtained by the calcination temperature between 1000° C.-1300° C., preferably 1200° C., are very effective. When this invention applied to a variety of foods, it was observed a high level antibacterial effect and so, it can be reliably used in very wide limits. Other than that, it was observed that calcium oxide is also extremely effective on cancer cells.

Aqueous Solution of Calcium Oxide (CaO),

The reaction results in the form of $CaO+H_2O \rightarrow CaOH+OH^-$, OH ions are released into the medium and these ions prevent growth of bacteria by breaking the cell walls of bacteria. Thus, CaO with high purity mentioned in the invention can be used in wide reliability for human health. Besides, Calcium oxide mentioned in the invention does not alter the taste and the smell of the foods.

The invention claimed is:

1. A production method of a calcium oxide compound with high purity, comprising:
   I. washing and drying a natural calcium oxide source,
   II. vibratory ball mill grinding the natural calcium oxide source, and
   III. calcinating the natural calcium oxide source in a rotary kiln using platinum as a catalyst and nitrogen to form an inert atmosphere at 700-1200° C. for 1-3 hours forming the calcium oxide compound with high purity.

2. A production method of a calcium oxide compound with high purity, comprising:
   I. washing and drying a natural calcium oxide source,
   II. vibratory ball mill grinding of the natural calcium oxide source,
   III. calcinating the natural calcium oxide source in a rotary kiln using platinum as a catalyst nitrogen to form an inert atmosphere at 1000-1400° C. for 1.5-2.5 hours forming the calcium oxide compound with high purity.

3. The production method of the calcium oxide compound with high purity as in claim 2, wherein the step III is conducted at 1150-1250° C. for 1 hour 45 minutes-2 hours 15 minutes.

4. The production method of the calcium oxide compound with high purity as in claim 3, wherein the step III is conducted at 1200° C. for 2 hours.

* * * * *